United States Patent
Rea et al.

(10) Patent No.: US 10,646,685 B2
(45) Date of Patent: May 12, 2020

(54) LUMINOUS ROOF FOR NICU INCUBATORS FOR REGULATING CIRCADIAN RHYTHMS IN INFANTS AND FOR PROVIDING HIGH VISIBILITY OF INFANT ANATOMY FOR HEALTHCARE STAFF

(71) Applicant: Rensselaer Polytechnic Institute, Troy, NY (US)

(72) Inventors: Mark S. Rea, Melrose, NY (US); Mariana Gross Figueiro, Troy, NY (US); Martin B. Overington, Germantown, NY (US); Jean Paul Freyssinier, Troy, NY (US); Robert White, Niles, MI (US)

(73) Assignee: Rensselaer Polytechnic Institute, Troy, NY (US)

( * ) Notice: Subject to any disclaimer, the term of this patent is extended or adjusted under 35 U.S.C. 154(b) by 350 days.

(21) Appl. No.: 15/309,571

(22) PCT Filed: Dec. 2, 2014

(86) PCT No.: PCT/US2014/068010
§ 371 (c)(1),
(2) Date: Nov. 8, 2016

(87) PCT Pub. No.: WO2015/171178
PCT Pub. Date: Nov. 12, 2015

(65) Prior Publication Data
US 2017/0182282 A1    Jun. 29, 2017

Related U.S. Application Data

(60) Provisional application No. 61/990,845, filed on May 9, 2014, provisional application No. 62/042,278, filed on Aug. 27, 2014.

(51) Int. Cl.
*A61M 21/00* (2006.01)
*H05B 37/02* (2006.01)
(Continued)

(52) U.S. Cl.
CPC ............. *A61M 21/00* (2013.01); *A61G 11/00* (2013.01); *A61N 5/0618* (2013.01);
(Continued)

(58) Field of Classification Search
CPC .................. A61G 11/00; A61N 5/0618; A61N 2005/0637; A61N 2005/0652;
(Continued)

(56) References Cited

U.S. PATENT DOCUMENTS

| | | |
|---|---|---|
| 8,409,073 B2 | 4/2013 | Ibara et al. |
| 8,779,681 B2 | 7/2014 | Adler |

(Continued)

FOREIGN PATENT DOCUMENTS

| | | |
|---|---|---|
| CN | 1928425 A | 3/2007 |
| CN | 101683296 A | 3/2010 |

(Continued)

OTHER PUBLICATIONS

International Search Report issued in PCT/US2014/068010 dated Mar. 13, 2015 (2 pages).
(Continued)

*Primary Examiner* — Navin Natnithithadha
*Assistant Examiner* — Sunita Reddy
(74) *Attorney, Agent, or Firm* — Murtha Cullina LLP; Anthony P. Gangemi

(57) ABSTRACT

Multipurpose lighting systems and methods of providing controllable lighting are provided. A lighting system includes a sheet of flexible material, a plurality of light sources and a controller. The plurality of light sources are attached to the sheet of flexible material and configured to
(Continued)

emit diffused light. The controller is coupled to the plurality of light sources and is configured to control one or more of the plurality of light sources according to one of a plurality of prescribed lighting characteristics associated with a respective plurality of different lighting tasks. In some examples, the lighting system includes a camera coupled to the sheet of flexible material configured to capture at least one image of an object synchronously with the light emitted by the plurality of light sources.

21 Claims, 10 Drawing Sheets

(51) Int. Cl.
    *H05B 33/08* (2020.01)
    *A61N 5/06* (2006.01)
    *A61G 11/00* (2006.01)
(52) U.S. Cl.
    CPC ....... *H05B 33/086* (2013.01); *H05B 33/0842* (2013.01); *H05B 37/0281* (2013.01); *A61M 2021/0044* (2013.01); *A61N 2005/0626* (2013.01); *A61N 2005/0637* (2013.01); *A61N 2005/0652* (2013.01); *A61N 2005/0662* (2013.01); *Y02B 20/42* (2013.01)
(58) Field of Classification Search
    CPC .... A61N 2005/0662; A61N 2005/0626; Y02B 20/42; H05B 33/086; H05B 37/0281; H05B 33/0842; A61M 21/00; A61M 2021/0044
    USPC .................................................. 600/26–28
    See application file for complete search history.

(56) References Cited

U.S. PATENT DOCUMENTS

| | | | |
|---|---|---|---|
| 2001/0028227 A1* | 10/2001 | Lys | A61N 5/0616 315/317 |
| 2003/0189829 A1* | 10/2003 | Shimizu | F21L 4/00 362/240 |
| 2004/0044384 A1* | 3/2004 | Leber | A61N 5/0619 607/88 |
| 2006/0089546 A1* | 4/2006 | Mahony | A61B 5/0064 600/310 |
| 2007/0053179 A1 | 3/2007 | Pang et al. | |
| 2008/0018244 A1 | 1/2008 | Anandan | |
| 2009/0109661 A1* | 4/2009 | Holderman | A47C 7/725 362/131 |
| 2010/0076248 A1 | 3/2010 | Ibara et al. | |
| 2010/0114263 A1* | 5/2010 | Pressler | A61N 5/0621 607/88 |
| 2011/0081527 A1* | 4/2011 | Yamato | H05K 3/386 428/195.1 |
| 2011/0175533 A1* | 7/2011 | Holman | E04B 9/32 315/130 |
| 2011/0203147 A1* | 8/2011 | Van Herpen | H05B 37/0227 40/541 |
| 2011/0313294 A1* | 12/2011 | de Roode | A61B 5/0059 600/473 |
| 2012/0253433 A1 | 10/2012 | Rosen et al. | |
| 2013/0006118 A1* | 1/2013 | Pan | A61N 5/0616 600/476 |
| 2013/0079661 A1* | 3/2013 | Tolosa | A61B 5/01 600/549 |
| 2013/0082298 A1* | 4/2013 | Golle | H01L 29/18 257/99 |
| 2014/0078301 A1* | 3/2014 | Fazzi | A61B 5/0059 348/143 |
| 2014/0212329 A1* | 7/2014 | Veen | A61G 11/00 422/4 |
| 2014/0221728 A1* | 8/2014 | Bodlaender | A61G 11/00 600/22 |
| 2015/0250978 A1* | 9/2015 | Pelsue | A61M 21/02 600/28 |
| 2015/0254964 A1* | 9/2015 | Raichman | G08B 21/245 340/573.1 |
| 2016/0157761 A1* | 6/2016 | De Haan | A61B 5/0059 600/315 |
| 2016/0235306 A1* | 8/2016 | Atallah | A61B 5/6892 |
| 2017/0125392 A1* | 5/2017 | Bibl | H01L 33/44 |

FOREIGN PATENT DOCUMENTS

| | | |
|---|---|---|
| CN | 103717964 A | 4/2014 |
| WO | 2013038288 A1 | 3/2013 |

OTHER PUBLICATIONS

Written Opinion of the International Searching Authority issued in PCT/US2014/068010 dated Mar. 13, 2015 (7 pages).

International Preliminary Report on Patentability and Written Opinion for International Application No. PCT/US2014/068010, dated Nov. 15, 2016, 8 pages.

Chinese Notification of First Office Action issued in Chinese Application No. 201480079677.7, dated Nov. 27, 2017, with translation, 16 pages.

Chinese Search Report issued in Chinese Application No. 201480079677.7, dated Nov. 16, 2017, with translation, 4 pages.

\* cited by examiner

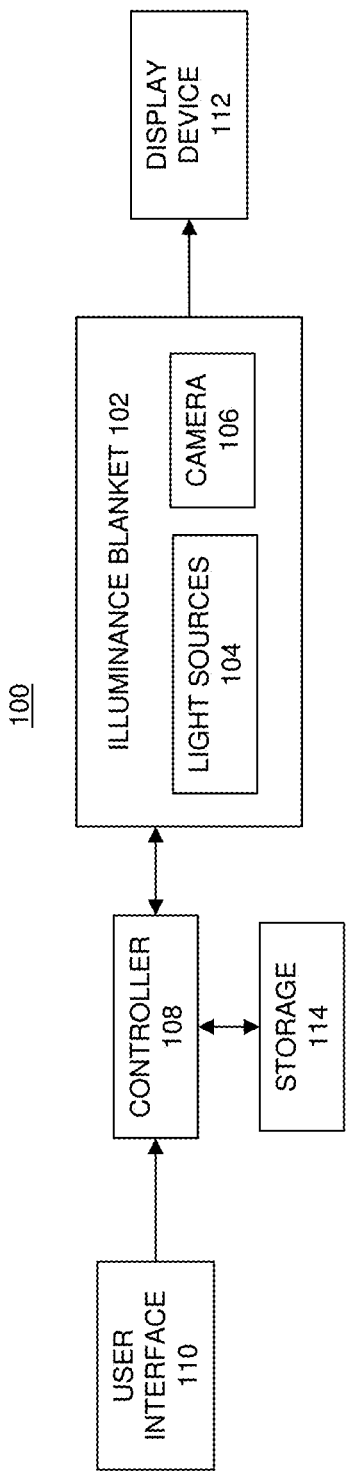
FIG. 1
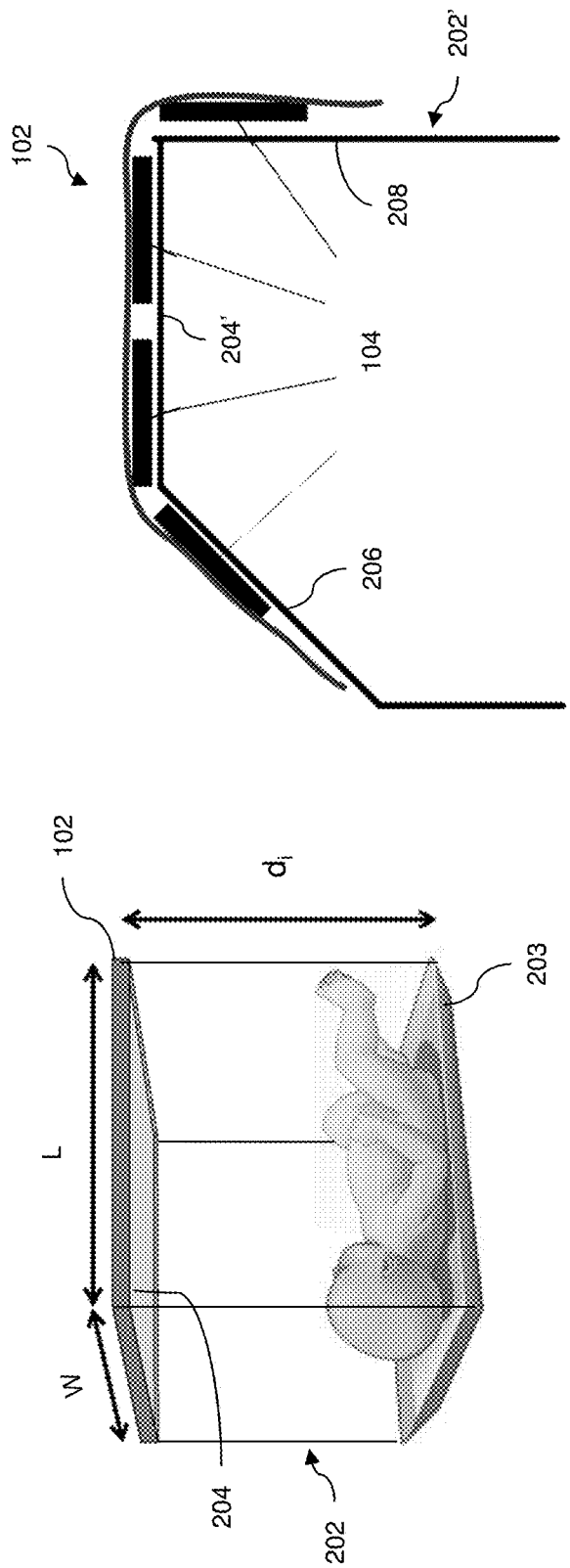
FIG. 2B
FIG. 2A

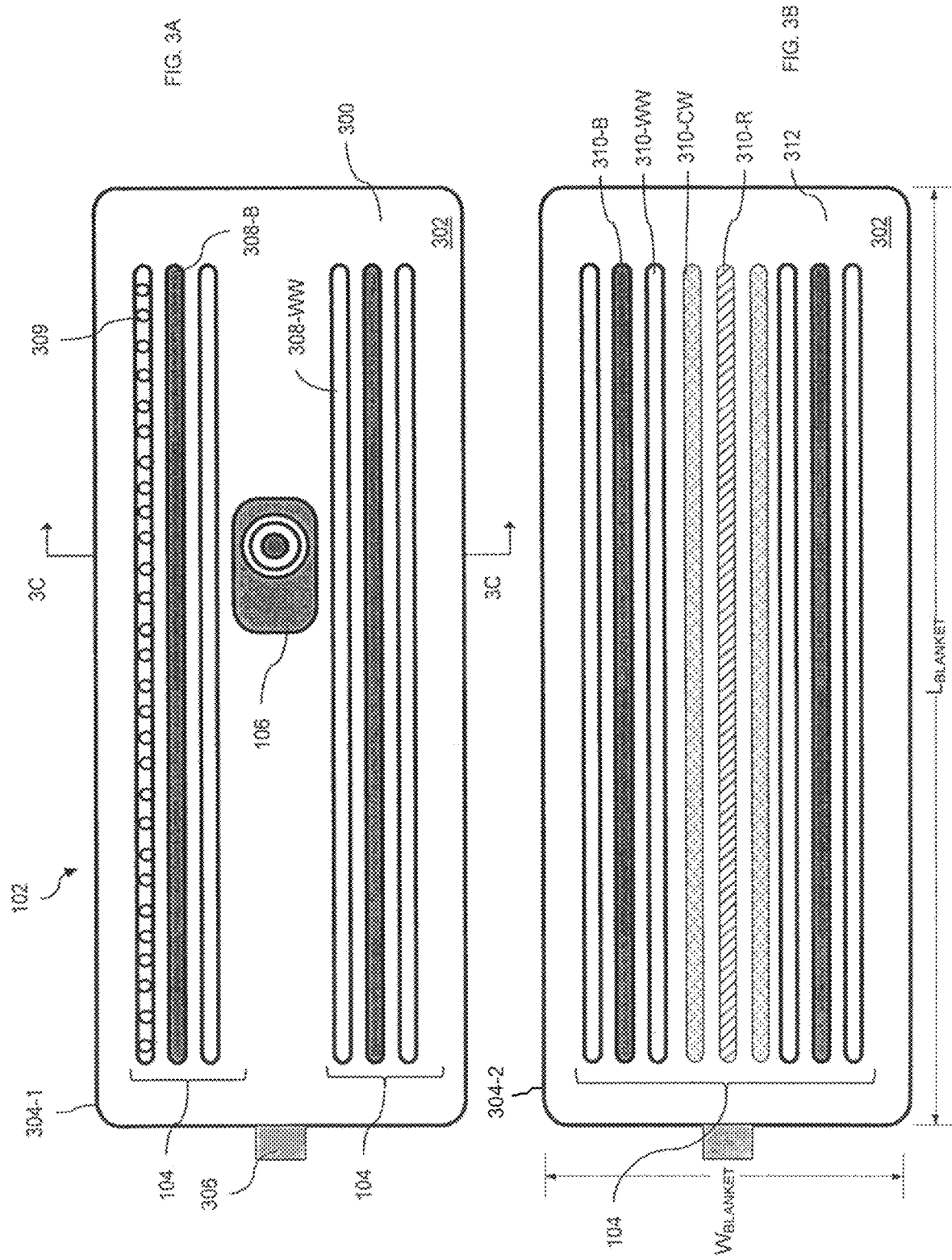

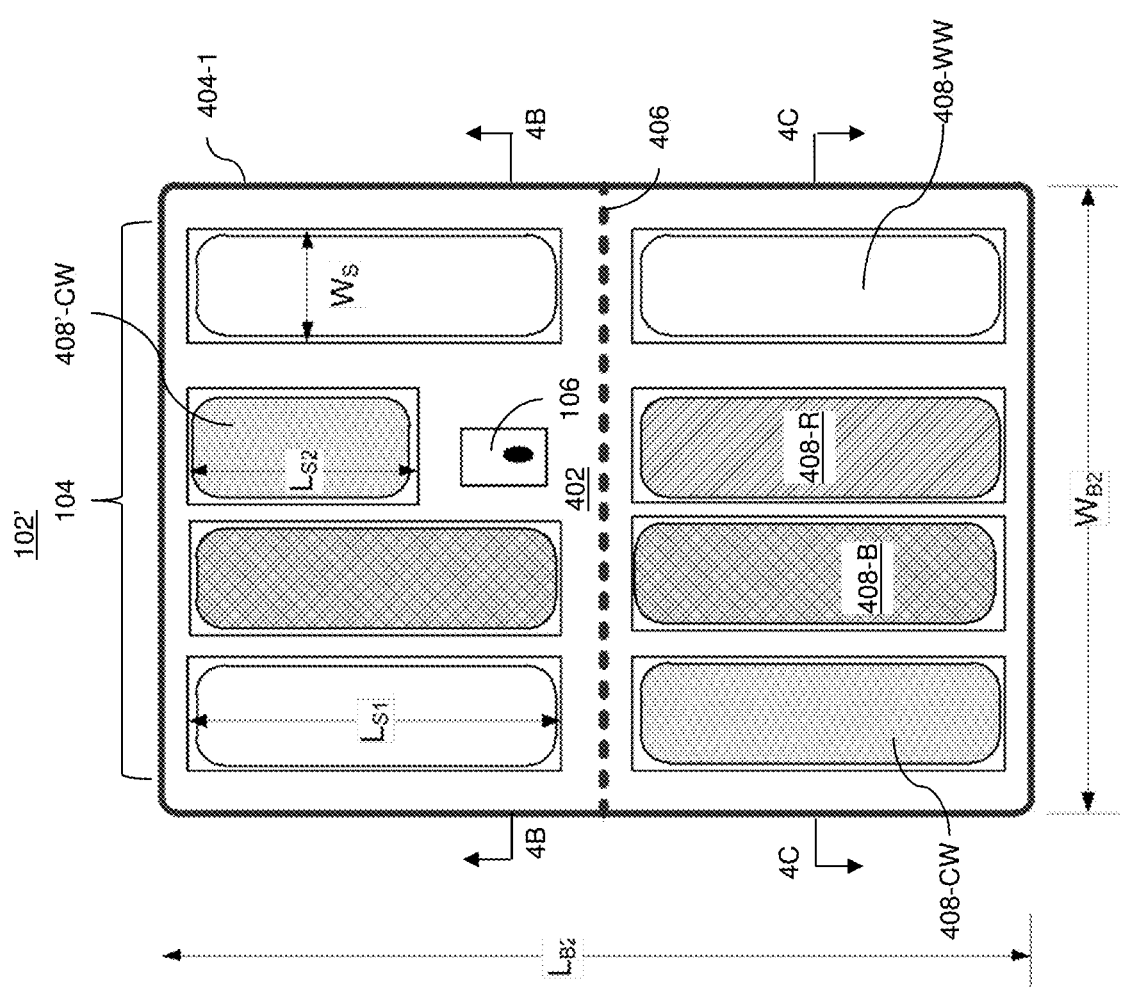

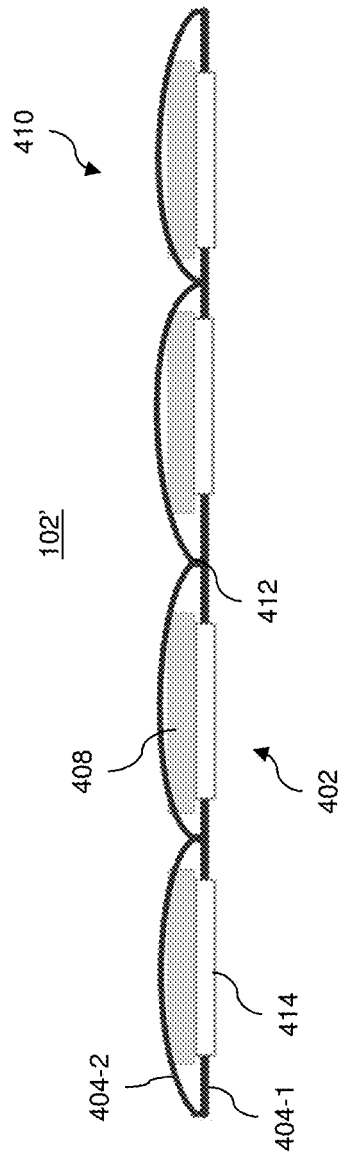
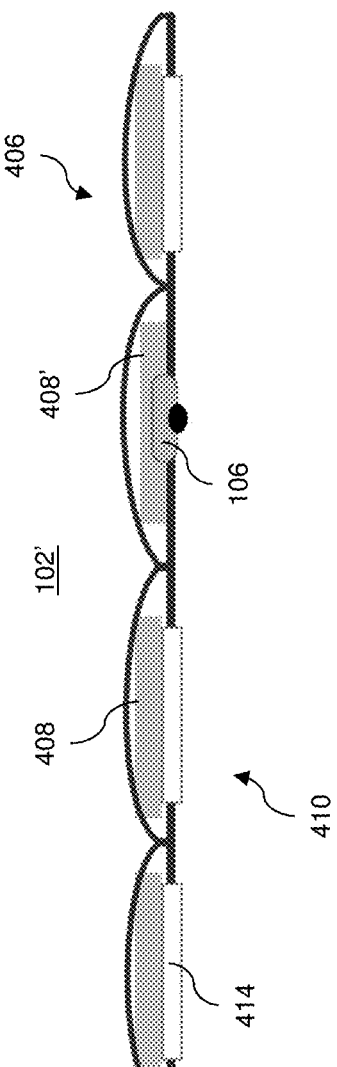

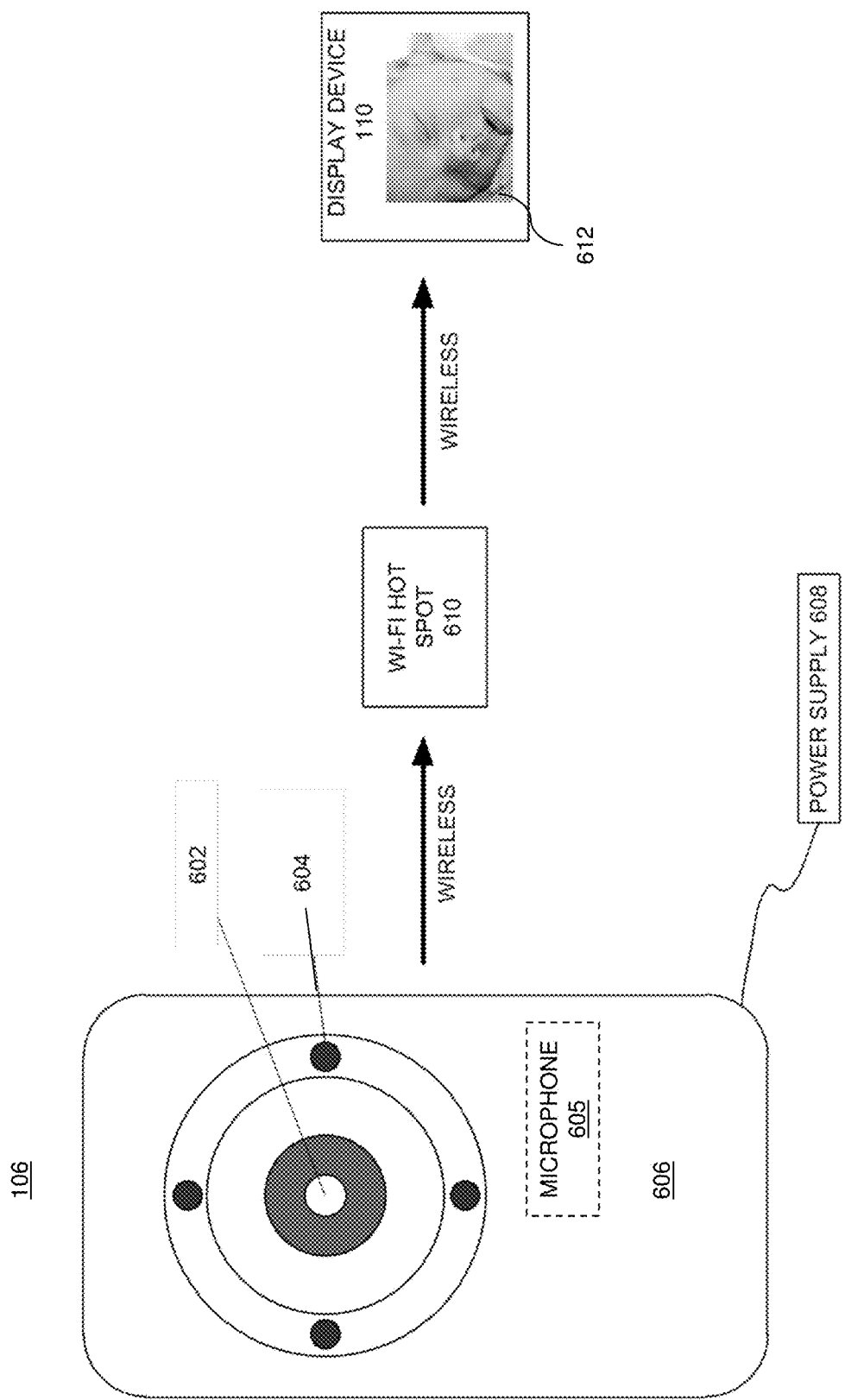

LUMINOUS ROOF FOR NICU INCUBATORS FOR REGULATING CIRCADIAN RHYTHMS IN INFANTS AND FOR PROVIDING HIGH VISIBILITY OF INFANT ANATOMY FOR HEALTHCARE STAFF

CROSS REFERENCE TO RELATED APPLICATIONS

This application is the U.S. National Phase Application of PCT/US2014/068010, filed Dec. 2, 2014, which is related to and claims the benefit of U.S. Provisional Application No. 61/990,845 entitled LUMINOUS ROOF FOR NICU INCUBATORS FOR REGULATING CIRCADIAN RHYTHMS IN INFANTS AND FOR PROVIDING HIGH VISIBILITY OF INFANT ANATOMY FOR HEALTHCARE STAFF, filed on May 9, 2014, and U.S. Provisional Application No. 62/042,278 entitled LUMINOUS ROOF FOR NICU INCUBATORS FOR REGULATING CIRCADIAN RHYTHMS IN INFANTS AND FOR PROVIDING HIGH VISIBILITY OF INFANT ANATOMY FOR HEALTHCARE STAFF, filed on Aug. 27, 2014, the contents of which are incorporated herein by reference.

STATEMENT REGARDING FEDERALLY SPONSORED RESEARCH

This invention was made with government support under R41HD078126-01 awarded by the National Institute of Health. The government has certain rights in this invention.

FIELD OF THE INVENTION

The present invention relates to the field of lighting systems for neonatal incubators, more specifically to multipurpose lighting systems and methods of controllable incubator lighting for multiple lighting tasks including regulating circadian rhythms in infants and providing high visibility of infant anatomy for healthcare staff.

BACKGROUND OF THE INVENTION

Neonatal intense care units (NICUs) provide specialized medical care to newborns immediately after birth and for as long as required, often several days or even weeks. While the care infants receive at any point during their stay at the NICU is very important, the first hour after birth, often referred to as the golden hour, is recognized as the most critical to their long term well-being. The level of specialization and training of the staff and the overall capabilities of the NICU facilities are crucial to achieving the medical needs of infants. In the US alone, approximately 100,000 newborns are placed in the NICU every year, with an average stay that ranges from 5.9 days for full term infants to 46.2 days for pre-term infants delivered at less than 32 weeks of gestation.

While the two most common reasons for admission to specialized care nurseries are preterm gestation and respiratory related symptoms, many infants are admitted for observation of other conditions, such as suspected infection, neonatal jaundice, hypoglycemia, and newborn septicemia. NICUs may be demanding and stressful environments where immediate response may be needed. In NICUs, visual cues provide much of information that caregivers rely upon to make decisions, perform functions (such as drawing blood) and monitor developmental changes. Thus, examination lights that facilitate quick and accurate visual functions are a fundamental tool in NICUs of any level of care. Lighting is also considered to be a significant environmental variable for promoting healthy development in newborns.

SUMMARY OF THE INVENTION

One aspect of the present invention relates to a lighting system. The lighting system includes a sheet of flexible material, a plurality of light sources and a controller. The plurality of light sources are attached to the sheet of flexible material and are configured to emit diffused light. The controller is coupled to the plurality of light sources. The controller is configured to control one or more of the plurality of light sources according to one of a plurality of prescribed lighting characteristics associated with a respective plurality of different lighting tasks.

Another aspect of the present invention relates to a method for providing controllable lighting. The method includes receiving, by a controller, an indication of a lighting task to be performed via an illuminance blanket. The illuminance blanket includes a plurality of light sources attached to a sheet of flexible material. The illuminance blanket is disposed in a vicinity of an object to be illuminated. The method also includes identifying, by the controller, a prescribed lighting characteristic associated with the indicated lighting task from among a plurality of prescribed lighting characteristics associated with a respective plurality of different lighting tasks; and controlling one or more of the plurality of light sources of the illuminance blanket to emit diffused light according to the identified prescribed lighting characteristic.

BRIEF DESCRIPTION OF THE DRAWINGS

The invention may be understood from the following detailed description when read in connection with the accompanying drawings. It is emphasized that, according to common practice, various features/elements of the drawings may not be drawn to scale. On the contrary, the dimensions of the various features/elements may be arbitrarily expanded or reduced for clarity. Moreover, in the drawings, common numerical references are used to represent like features/elements. Included in the drawing are the following figures:

FIG. 1 is a functional block diagram of an example multipurpose lighting system including an illuminance blanket for different lighting tasks, according to an aspect of the present invention;

FIG. 2A is a perspective view diagram of an example illuminance blanket of FIG. 1 disposed on an incubator, according to an aspect of the present invention;

FIG. 2B is a perspective view diagram of an example illuminance blanket of FIG. 1 disposed on an incubator, according to another aspect of the present invention;

FIG. 3A is a bottom view diagram of an example illuminance blanket shown in FIG. 1, according to an aspect of the present invention;

FIG. 3B is an top view diagram of the example illuminance blanket shown in FIG. 3A, according to an aspect of the present invention;

FIG. 4A is a bottom view diagram of an example illuminance blanket shown in FIG. 1, according to another aspect of the present invention;

FIG. 4B is a cross section view diagram of the example illuminance blanket shown in FIG. 4A along line 4B-4B, according to an aspect of the present invention;

FIG. 4C is a cross section view diagram of the example illuminance blanket shown in FIG. 4A along line 4C-4C, according to an aspect of the present invention;

FIG. 6 is a functional block diagram of an example camera shown in FIG. 1, illustrating an example wireless connection of the camera to a display device, according to an aspect of the present invention;

DETAILED DESCRIPTION OF THE INVENTION

Figure 3C:
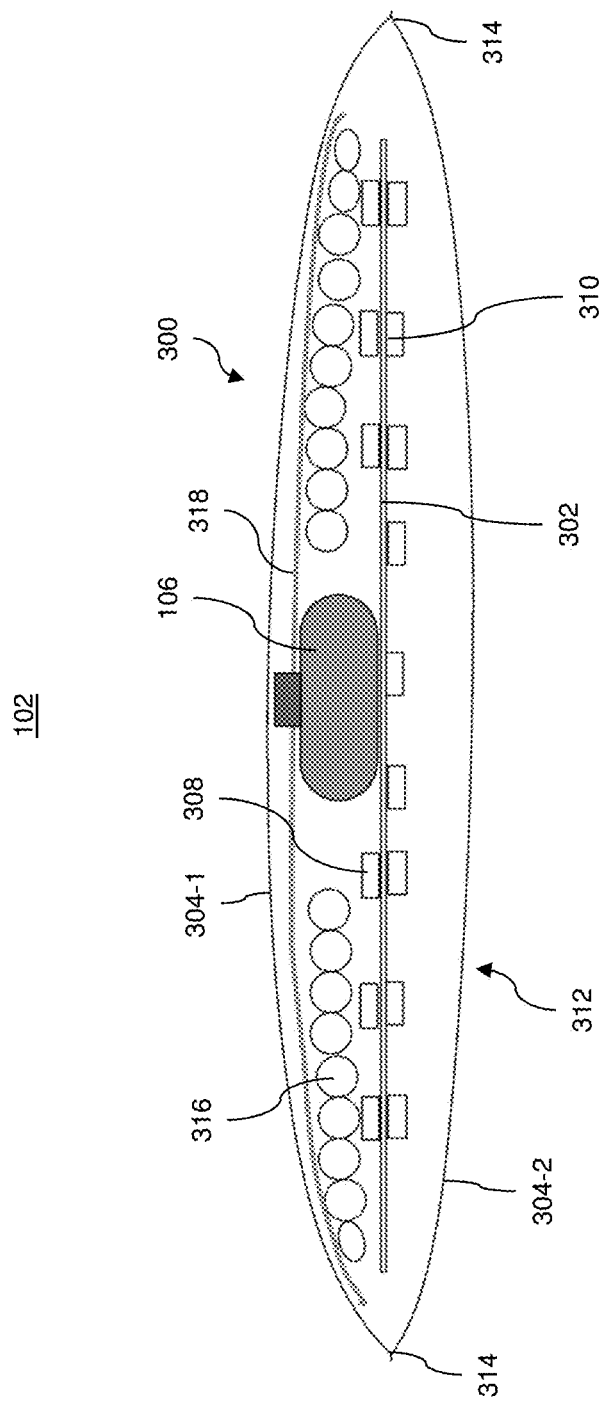
FIG. 3C is a cross section view diagram of the example illuminance blanket shown in FIG. 3A along line 3C-3C, according to an aspect of the present invention.

Incubators have been in use since the $19^{th}$ century, and have significantly improved survival for premature infants. However, incubator lighting systems can still be improved. For example, the lighting needs (e.g., amount, spectrum, distribution) of an infant are often in conflict with those of healthcare staff. In addition, the lighting needs (e.g., amount, spectrum, distribution) for healthcare staff are not typically ideal for viewing and attending to the infant. Furthermore, circadian rhythm formation and entrainment in infants is not addressed by current lighting systems in the NICU.

Aspects of the invention relate to multipurpose lighting systems and methods of lighting for different lighting tasks. An example lighting system includes a sheet of flexible material, a plurality of light sources attached to the sheet of flexible material and a controller coupled to the plurality of light sources. The plurality of light sources are configured to emit diffused (i.e., shadow-free) light. The controller is configured to control one or more of the plurality of light sources according to one of a plurality of prescribed lighting characteristics associated with a respective plurality of different lighting tasks. In some examples, the sheet of flexible material and the plurality of light sources may be formed as an illuminance blanket. In some examples, a camera may also be disposed on the illuminance blanket, in the vicinity of the light sources, to capture one or more images of an object (e.g., an infant in an incubator). In some examples, the captured image(s) may be provided to a display device that may be remote from the lighting system. In some examples, the light sources include light-emitting diodes (LEDs). In some examples, the controller may control at least one of an intensity, a color (i.e., a spectrum), a distribution, a timing or a duration of one or more of the light sources according to the prescribed lighting characteristic.

In some examples, the lighting system includes a solid state lighting (SSL) system for use with NICU incubators. In some examples, the illuminance blanket may be removably coupled to an incubator. For example, the illuminance blanket may be removably disposed on a top surface of an incubator, to emit diffused light into the incubator. In some examples, the illuminance blanket may include a transparent cover formed from a skid-resistant material.

The plurality of prescribed lighting characteristics may include lighting characteristics that promote circadian entrainment in premature infants (e.g., a correct amount, spectrum, time and duration). The prescribed lighting characteristics may also include those which provide excellent visibility of infant anatomy for nurses and physicians during critical tasks (e.g., insertion of an intravenous (IV) catheter). Other prescribed lighting characteristics may include those which provide general illumination in the incubator for direct and/or remote viewing (e.g., with an infrared camera) for families and/or caregivers.

The controller of the lighting system may control the prescribed lighting characteristic of the illumination provided by the illuminance blanket. The prescribed lighting characteristic may include an intensity, a distribution, a spectrum, a duration, a timing or any combination thereof. The illuminance blanket (via the plurality of light sources) may provide illumination adaptable to multiple scenarios, including in-room examination, remote observation via a digital sensing camera, direct skin examination, vein detection for catheter and needle administration, administration of critical medical procedures (i.e., any medical procedure where shadow-free light and color are important for visibility) and circadian entrainment.

The plurality of light sources may provide excellent color rendering for some lighting tasks (such as for direct and/or remote viewing). For other tasks, such as insertion of an IV catheter, restricted spectra may provide better contrast of the vein. Thus, the lighting system may change the spectral content, via the controller, to enhance chromatic information for some lighting tasks.

In some examples, the lighting system provides illumination to the incubator that supports direct and remote viewing (via a camera integrated into the illuminance blanket). Creating a high-fidelity visual connection between family members who cannot be at the bedside and the premature infant is becoming increasingly important. Remote viewing of the infant may also be desirable for staff members, who are often unable to directly assess the status of the infant (because the incubator may be covered with a blanket or because it may be inconvenient to view an infant in a private room). In some examples, a spectral power distribution of the plurality of light sources providing general illumination and a spectral response of the camera may be optimized to provide high color fidelity images of the infant at one or more remote locations.

As discussed above, current incubators do not address the development and entrainment of circadian rhythms in infants. The suprachiasmatic nuclei, where the biological clock is located, are functional early in the third trimester. Consequently, cycled lighting may improve a weight gain in preterm infants and may reduce a length of stay of preterm infants in the NICU. An example multipurpose lighting system may promote circadian entrainment through a prescribed lighting characteristic including controlled cycled light of the appropriate spectrum, intensity, duration and timing.

An example multipurpose lighting system may provide shadow-free illumination to support the performance of critical visual tasks (e.g., medical procedures). For example, for inserting IV catheters and performing other critical tasks (e.g., drawing blood), it may be desirable to deliver high-intensity light to a small area of an infant. In some examples, higher intensity (critical task) light may be delivered by the lighting system without spill-light entering the infant's eyes or those of adjacent infants. In some examples, the infant's eyes may be shaded during critical task procedures. The lighting system may control the distribution, spectrum and intensity of the light sources according to a prescribed lighting characteristic associated with a critical medical procedure.

In some examples, the multipurpose lighting system may be configured to conform to current NICU lighting standards (flicker, color rendering index (CRI) and light level standards), such as standards stated by the Eighth Consensus on Newborn NICU Design, Clearwater Beach, Fla., Jan. 26, 2012. These current standards provide, for example, recommended flicker, color rendering index and light level standards for newborn infants. For example, Standard 22 of the Eighth Consensus ("Ambient Lighting in Infant Care Areas") recommends a maximum ambient lighting level of 600 lux, that electric light sources have a CRI of no less than 80, a gamut area index (GAO of no less than 80 and no greater than 100 and that a lamp source does not flicker more than a common 40 W incandescent light source. Standard 23 of the Eighth Consensus ("Procedure Lighting in Infant Care Areas") recommends a minimum of 2000 lux at the plane of the infant bed.

Example multipurpose lighting systems may address the lighting needs of both the infant and the healthcare provider. An example illuminance blanket of the lighting system may be used with blanket covers on incubators that are commonly used in the NICU. Example illuminance blankets may be formed for use with any incubator. Example lighting systems may provide circadian entraining light (i.e., a suitable amount, spectrum, time and duration) to an infant, excellent color rendering (defined by high CRI and high GAI) for healthcare providers, diffuse (i.e., shadow-free light) of sufficient level for excellent visibility for healthcare providers and a camera (for example with an infrared source) for continuous monitoring of the infant. By incorporating a camera into the illuminance blanket, the amount of extra equipment needed inside the incubator is reduced. Because the illuminance blanket may be flexible (and in some examples may be foldable), as well as removably disposed on the incubator, the illuminance blanket may be easy to apply to the incubator, adjust and store (e.g., when not in use).

Although the description herein describes a multipurpose light for NICU incubators, the lighting system may also be used with any object where prescribed lighting characteristics for different lighting tasks may be desirable. It is contemplated that the lighting system may be used, for example, without being limited to, in under cabinet lighting, for aquariums/terrariums (for regulating circadian rhythms in fish/reptiles and for providing suitable visibility), for food displays, for photography lighting, for emergency medical service(s) (EMS) lighting and for portable work lighting.

Referring to FIG. 1, a functional block diagram of an example multipurpose lighting system 100 is shown. System 100 may include illuminance blanket 102, controller 108, user interface 110, display device 112 and storage 114. Although storage 114 is illustrated as being separate from, and coupled to, controller 108, in some examples, storage 114 may be part of controller 108 (such as storage 508 shown in FIG. 5A). Storage 114 may store a plurality of prescribed lighting characteristics associated with a respective plurality of different lighting tasks.

Illuminance blanket 102 may include plurality of light sources 104 and camera 106 integrated within illuminance blanket 102. In general, illuminance blanket 102 includes light sources 104 attached to a sheet of flexible material, such as sheet 302 (FIG. 3C) or cover 404-1 (FIG. 4B). In general, illuminance blanket 102 may be configured to be flexible and/or foldable, such that illuminance blanket 102 may conform to a surface on which it is disposed.

Camera 106 may be attached to illuminance blanket 102 in a vicinity of light sources 104 (such as shown in FIGS. 3A and 4A). Camera 106 may capture one or more images of an infant in an incubator (such as incubator 202 in FIG. 2A) with the illumination (i.e., prescribed lighting characteristic) provided by light sources 104. In some examples, camera 106 may also include an infrared (IR) light source to capture one or more images of the infant using infrared radiation (e.g., between about 700 nm to about 1 mm). IR imaging (also referred to as thermal imaging) may be useful in low visible light environments (e.g., for visible light intensity less than about 1 lux. In some examples, camera 106 may be configured to process the captured image(s), such as to detect infant motion. In some examples, image(s) from camera 106 may be stored in storage 114. Camera 106 is described further below with respect to FIG. 6.

Referring to FIGS. 2A and 2B, illuminance blanket 102 may be removably disposed on top surface 204 (204') of incubator 202 (202'). Incubator 202' (FIG. 2B) is similar to incubator 202 (FIG. 2A) except that incubator 202' includes sloped front wall 206. In some examples, illuminance blanket 102 may be formed in a rectangular shape having width (W) and length (L) to correspond to a top surface of an incubator, such as top surface 204 of incubator 202 (FIG. 2). In some examples, illuminance blanket 102 may fully cover top surface 204 of incubator 202, without extending to other surfaces of incubator 202. In some examples, illuminance blanket 102 may extend over top surface 204 of incubator 202 and cover a portion of other surfaces. For example illuminance blanket 102 may extend over sloped front wall 206 and/or rear wall 208 of incubator 202' (FIG. 2B). In some examples, illuminance blanket 102 may not completely cover top surface 204, 204' (not shown in FIGS. 2A and 2B). It is understood that incubators 202, 202' represent examples of incubators and that an incubator may have other suitable shapes. In general, illuminance blanket 102 may be formed to cover at least a portion of top surface 204 (204') of incubator 202 (202'), such that illuminance blanket 102 is at a distance $d_i$ from bottom surface 203 of incubator 202.

In one example, illuminance blanket 102 has a length L of about 60 cm and a width W of about 30 cm, and is at a distance $d_i$ between about 35 cm to about 50 cm from bottom surface 203. It is understood that the dimensions given for illuminance blanket 102 and the distance $d_i$ of illuminance blanket 102 from bottom surface 203 represent examples values. In other examples, illuminance blanket 102 may have different dimensions L, W and distance $d_i$ may be other values. In general, the prescribed lighting characteristic for a lighting task may be a function of the dimensions of illuminance blanket 102 and its distance $d_i$ from bottom surface 203.

In some examples, illuminance blanket 102 may have light sources 104 arranged to emit light from one side of illuminance blanket. In some examples, illuminance blanket 102 may have light sources 104 arranged to emit light from opposite sides of illuminance blanket. FIGS. 3A-3C describe one example of illuminance blanket 102 having light sources 308 and 310 on opposite sides of sheet 302. FIGS. 4A-4C describe another example of illuminance blanket 102' having light sources 408 that emit light from one side (from openings 414 in cover 404-1). Illuminance blanket 102 is described further below with respect to FIGS. 3A-4C. In some examples, light sources 104 are LEDs. Although light sources 104 are described herein with respect to LEDs, light sources 104 may include any suitable light sources capable of providing diffused light of sufficient spectral and spatial characteristics (i.e., a prescribed lighting characteristic) suitable for a corresponding lighting task.

Referring back to FIG. 1, controller 108 may be coupled to light sources 104 and to user interface 110. Controller 108 may receive an indication from user interface 110 regarding a selected lighting task and/or prescribed lighting characteristic. Responsive to the indication, controller 108 may control operation of one or more of light sources 104 to emit light according to a prescribed lighting characteristic associated with the indication. The prescribed lighting characteristic may control at least one of an intensity, a spectrum, a distribution, a duration or a timing of the emitted light by light source(s) 104. Example lighting tasks may include in-room examination, remote observation via display device 112, direct skin examination, vein detection, administration of one or more medical procedures and circadian entrainment. Depending upon the desired lighting task, controller 108 may control one or more light sources 104 of illuminance blanket 102 to produce diffuse, general illumination for circadian entrainment; diffuse, general illumination for-room and remote viewing; chromatically enhanced illumination for cyanosis observation and/or vein enhancement; or diffuse high light level illumination for medical procedures. For example, by controlling activation of the number of light sources 104, the electrical power to light source(s) 104, or the light transmission of any diffuser material (e.g., cushioning material 316 and/or diffuser material 318 in FIG. 3C) disposed on light sources 104, high light levels (e.g., about 2000 lx) may be provided during medical procedures without causing sharp shadows or glare to the practitioner.

Controller 108 may also be configured to control operation of camera 106 to capture one or more images of an infant under sufficient visible light conditions and/or under low visible light conditions. Controller 108 may control operation of camera 106 based on an indication received from user interface 110 and/or based on predetermined automatic conditions for capture (e.g., one image every 10 mins., a video stream from a predetermined onset time to a predetermined end time, etc.). Controller 108 may also control transmission of image(s) from camera 106 to one or more display devices 112. (Although one display device 112 is shown, lighting system 100 may include two or more display devices 112).

Figure 5A:
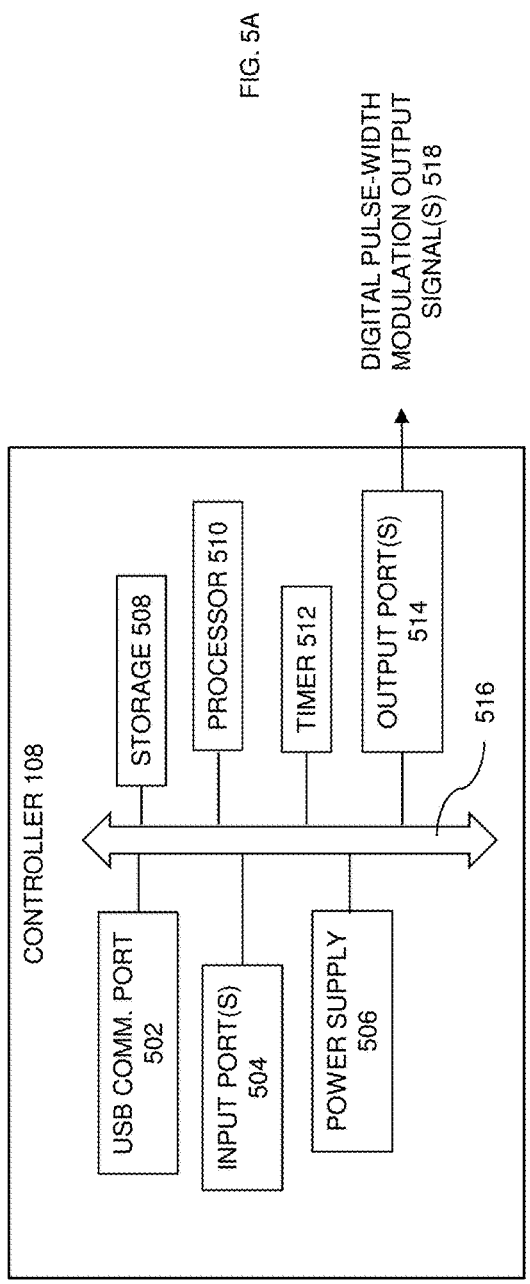
FIG. 5A is a functional block diagram of an example controller shown in FIG. 1, according to an aspect of the present invention.

In some examples, controller 108 may be configured to process image(s) and/or audio information received from camera 106 (such as via processor 510 in FIG. 5A). For example, controller 108 may detect infant motion based on multiple images received from camera 106. As another example, controller 108 may identify a change in infant state (e.g., from asleep to awake) based on crying or other sounds detected from audio information. In some examples, controller 108 may provide an indication (e.g., visual, audible, haptic, etc.) of the infant's behavior to a caregiver via a suitable user interface (such as display device 112). In some examples, both visual movement (from captured images) and sound(s) (from captured audio information) may be used to identify the infant's behavior.

In some examples, controller 108 may verify the lighting characteristics of the light actually delivered by light sources 104 as well as a time stamp of the delivery time (or time period) (such as via processor 510 in FIG. 5A). Controller 108 may cause storage 114 to store an indication of the verification and/or the time stamp (time period) for the emitted light. Controller 108 is described further below with respect to FIGS. 5A and 5B.

User interface 110 may be configured to control selection of the prescribed lighting characteristic applied by controller 108 to light source(s) 104. User interface 110 may include any suitable interface for directly selecting a prescribed lighting characteristic or a desired lighting task (associated with a prescribed lighting characteristic). In some examples, user interface 110 may also be used to control image/video capture by camera 106 (including daytime or nighttime image/video capture) and/or transmission of the captured image/video to a particular display device 112. In some examples, user interface 110 may include an input device such as a keypad for selecting the prescribed lighting characteristic/lighting task. In some examples, user interface 110 may include a display device for reviewing possible lighting characteristic/lighting task selection.

Display device 112 may be located remote from illuminance blanket 102. Display device 112 may be wired or wirelessly connected to camera 106, to display one or more images (including a video stream) captured by camera 106. It is contemplated that display device 112 may include any display device capable of presenting images and/or video. For example, display device 112 may include a personal computer, a portable computer, a tablet computer, a mobile phone, etc. Display device 112 may be used to provide remote viewing of an infant in incubator 202. Although one display device 112 is shown in FIG. 1, it is understood that illuminance blanket 102 may be coupled to one or more display devices 112. For example, a first display device 112 may be provided to a healthcare provider while a second display device 112 may be provided to a family member of the infant.

In some examples, controller 108 and user interface 110 may be located remote from illuminance blanket 102. In some examples, controller 108 and/or user interface 110 may be located on illuminance blanket 102.

It is contemplated that system 100 may be configured to connect to a global information network, e.g., the Internet, (not shown) such that images/video may be transmitted to display device 112 and/or to another remote location for further processing and/or storage.

In some examples, camera 106 may include a microphone (e.g., microphone 605 in FIG. 6) to capture audio information from the infant for storage and processing. The audio may also be transmitted to display device 112 or another suitable device capable of outputting an audio signal. In this manner, both the visual and auditory signs of the infant may be remotely monitored. In some examples, the audio information may be stored in storage 114.

Storage 114 may store a plurality of prescribed lighting characteristics associated with a respective plurality of different lighting tasks. In some examples, storage 114 may store one or more images and/or audio information captured via camera 106. Storage 114 may include, for example, a random access memory (RAM), a magnetic disk, an optical disc, flash memory or a hard drive). In general, storage 114 may be a memory, a magnetic disk, a database or essentially any local or remote non-transitory, tangible device capable of storing data. In some examples, controller 108 (and/or storage 114) may receive prescribed lighting characteristics from a remote device (not shown) coupled to controller 108 (such as via port 502 and/or port 504 shown in FIG. 5A) and/or coupled to storage 114.

It is understood that components of one or more of camera 106, controller 108, user interface 110, display device 112 and storage 114 may be implemented in hardware, software or a combination of hardware and software.

Referring to FIGS. 3A-3C, example illuminance blanket 102 is shown. In particular, FIG. 3A is a bottom view diagram of illuminance blanket 102 illustrating bottom surface 300; FIG. 3B is a top view diagram of illuminance blanket 102 illustrating top surface 312; and FIG. 3C is a cross section view diagram of illuminance blanket 102 along line 3C-3C.

As shown in FIG. 3A, bottom surface 300 of illuminance blanket 102 includes plurality of light sources 104 disposed on flexible sheet 302 of transparent material. Bottom surface 300 also includes camera 106 disposed on flexible sheet 302 in the vicinity of light sources 104. Flexible sheet 302 is formed in a rectangular shape, for example, to conform to a top surface of an incubator. Cover 304-1 of transparent material is disposed over light sources 104 and camera 106. In an example, illuminance blanket 102 has a width $W_{BLANKET}$ of about 30 cm and a length $L_{BLANKET}$ of about 60 cm.

In an example, both flexible sheet 302 and cover 304-1 (as well as cover 304-2) are formed from 16 gauge clear vinyl material. Although sheet 302 and covers 304-1, 304-2 are illustrated as being formed from a same material, sheet 302 and covers 304-1, 304-2 may be formed from different material. Although sheet 302 is described as being transparent, in some examples, sheet 302 may be formed from opaque material, to reduce transmission of light through to an opposite side. For example, an opaque sheet 302 may reduce the transmission of light directed from bottom surface 302 (by light strips 308) through to top surface 312. In general, sheet 302 and covers 304-1, 304-2 may be formed from any suitable flexible material capable of conforming to a shape of an object upon which it is disposed.

In some examples, covers 304-1, 304-2 may include skid-resistant material, to prevent illuminance blanket 102 from slipping off of a surface, such as top surface 204 of incubator 202 (FIG. 2A). In some examples, covers 304-1, 304-2 may be formed from a medical grade anti-microbial material. In some examples, covers 304-1, 304-2 may be formed from a fluid-proof medical grade material.

Illuminance blanket 102 also includes electrical connector 306 for electrically coupling controller 108 (FIG. 1) to light sources 104. Connector 306 may also electrically couple controller 108 to camera 106. For clarity, electrical leads between light sources 104, camera 106 and electrical connector 106 are not shown.

Light sources 104 on bottom surface 300 include plural light strips 308 having LEDs 309 arranged along each light strip 308. In an example, light strips 308 are configured to produce a maximum light intensity of 600 lux. In an example, light strips 308 include light strips 308-B having blue (B) LEDs (e.g., with a peak wavelength range between about 450 nm to 500 nm) and light strips 308-WW having warm white (WW) LEDs (having about 3,500 K correlated color temperature).

As shown in FIG. 3B, top surface 312 of illuminance blanket 102 includes plurality of light sources 104 (light strips 310) disposed on flexible sheet 302, but does not include camera 106. Cover 304-2 of transparent material is disposed over light strips 310. Light strips 310 are similar to light strips 308 (on bottom surface 302) except that light strips 310 are configured to provide a higher maximum light intensity than light strips 308, for example, about 2000 lux. In some examples, light strips 310 may be controlled to provide higher light intensity for various medical procedures.

In an example, light strips 310 include light strips 310-B having blue LEDs, light strips 310-CW having cool white (CW) LEDs (with greater than about 4,500 K correlated color temperature), light strips 310-R having red (R) LEDs (e.g., with a peak wavelength range between about 620 nm to about 650 nm) and light strips 310-WW having warm white LEDs.

Figure 8:
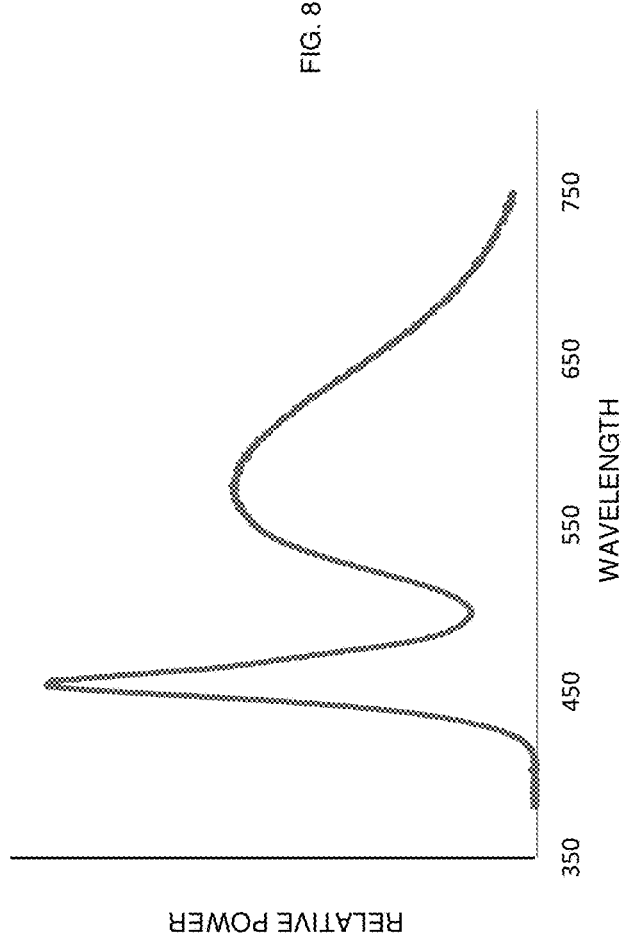
FIG. 8 is a graph of an example power distribution as a function of wavelength for the illuminance blankets shown in FIGS. 3A-3C and FIGS. 4A-4C, according to an aspect of the present invention.

Light strips 308 on bottom surface 300 and light strips 310 on top surface 312 may be controlled by controller 108 (FIG. 1) to produce different prescribed lighting characteristics associated with different lighting tasks. Example prescribed lighting characteristics are shown further below in Table 1. It is understood that the arrangement of blue, red, cool white and warm white LEDs in FIGS. 3A and 3B represent an example arrangement and that other arrangements of LEDs of different colors and/or intensity are possible. In some examples, one or more red light strips 310-R may be used for chromatic enhancement (e.g., for vein detection). In an example, LED strips 308, 310 include LED flex strips R6030 manufactured by LED Supply (Randolph, Vt.). One or more LEDs 309 among blue LED strips 308 (310)-B, red LED strips 310-R, cool white LED strips 310-CW, warm white LED strips 308 (310)-WW or a combination thereof may be activated to produce a desired color, distribution and intensity for a prescribed lighting characteristic. FIG. 8 is a graph illustrating an example spectral power distribution for cool white light strips 310-CW.

As shown in FIG. 3C, bottom cover 304-1 may be joined to top cover 304-2 at joints 314 (e.g., via an adhesive material). In some examples, illuminance blanket may include cushioning material 316. Cushioning material 316 may include, for example, an inflatable bubble wrap product, loose fill material, foam structures (e.g., polymeric foam structures), or any other suitable cushioning material. In some examples, cushioning material may include transparent cushioning material.

In some examples, illuminance blanket 102 may include diffusion material 318 between light strips 308 (and/or light strips 310) and cover 304-1 (and or cover 304-2). Diffusion material 318 may be formed from any suitable material capable of dispersing the light emitted by light strips 308 and/or light strips 310. In an example, diffusion material 318 includes a diffusing gel (Lee Filter 216) manufactured by Rosco Laboratories (Stanford, Conn.). Cushioning material 316 may act as a spacer between diffusion material 318 and light strips 308 (and/or light strips 310). In general, illuminance blanket 102 may include any spacer material disposed between flexible sheet 302 and diffusion material 318, such that light strips 308 (310) are spaced apart from diffusion material 318, to encourage diffusion via diffusion material 318.

Although FIGS. 3A-3C illustrate LEDs 308 and LEDs 310 on opposite sides of flexible sheet 302, in some examples, LEDs 308, LEDs 310 and camera 106 may all be disposed on the same side of flexible sheet 302, for example, bottom side 300.

Referring to FIGS. 4A-4C, example illuminance blanket 102' is shown. In particular, FIG. 4A is a bottom view diagram of illuminance blanket 102' illustrating bottom surface 402; FIG. 4B is a cross section view diagram of illuminance blanket 102' along line 4B-4B; and FIG. 4C is a cross section view diagram of illuminance blanket 102' along line 4C-4C. Illuminance blanket 102' is similar to illuminance blanket 102 (FIGS. 3A-3C) except that illuminance blanket 102' includes LED light panels 408, 408' that are disposed only on bottom surface 402 of illuminance blanket 102'. Although not shown in FIGS. 4A-4C, illuminance blanket 102' may include an electrical connector for electrically connecting controller 108 (FIG. 1) with light sources 104 as well as with camera 106.

As shown in FIGS. 4A-4C, bottom surface 402 of illuminance blanket 102' includes plurality of light sources 104 disposed under flexible cover 404-1 of transparent material. Cover 404-1 (and cover 404-2) may be foldable along dashed line 406. Bottom surface 402 also includes camera 106 disposed under cover 404-1 in the vicinity of light sources 104. Cover 404-1 is formed in a rectangular shape, for example, to conform to a top surface of an incubator. Light sources 104 include LED light panels 408 and light panel 408'. Light panel 408' is similar to light panel 408, except that light panel 408' is smaller in length to accommodate camera 106. In an example embodiment, light panels 408, 408' have a width $W_s$ of about 10 cm, light panel 408 has a length $L_{S1}$ of about 33 cm and light panel 408' has a length $L_{S2}$ of about 20 cm.

Covers 404-1, 404-2 are formed of a transparent material with light sources 408, 408' and camera 106 disposed between covers 404-1 and 404-2. Cover 404-1 includes apertures 414 for exposing light sources 408, 408' and camera 106 at bottom surface 402. Cover 404-1 is joined to cover 404-2 at joints 412 (for example with an adhesive material) between light sources 408, 408'. In an example, illuminance blanket 102' has a width $W_{B2}$ of about 56 cm and a length $L_{B2}$ of about 79 cm. In addition to fold 406, illuminance blanket 102' may also be foldable along joints 412.

In an example, covers 404-1, 404-2 are formed from a marine grade vinyl fabric material. Although covers 404-1, 404-2 are illustrated as being formed from a same material, covers 404-1, 404-2 may be formed from different material. Although cover 404-2 of top surface 410 is described as being transparent, in some examples, cover 404-2 may be formed form opaque material, to reduce transmission of light through top surface 410. In general, covers 404-1, 404-2 may be formed from any suitable flexible material capable of conforming to a shape of an object upon which it is disposed.

In some examples, covers 404-1, 404-2 may include skid-resistant material. In some examples, covers 404-1, 404-2 may be formed from a medical grade anti-microbial material. In some examples, covers 404-1, 404-2 may be formed from a fluid-proof medical grade material.

In an example, light panels 408, 408' include light panels 408-WW having warm white (WW) LEDs, light panels 408-CW, 408'-CW having cool white (CW) LEDs, light panels 408-B having blue (B) LEDs and light panel 408-R having red (R) LEDs. In an example, LED light panels 408, 408' include LumiSheet™ LED light panels (manufactured by Evo-lite, LLC of Denver, Colo.).

Figure 9:
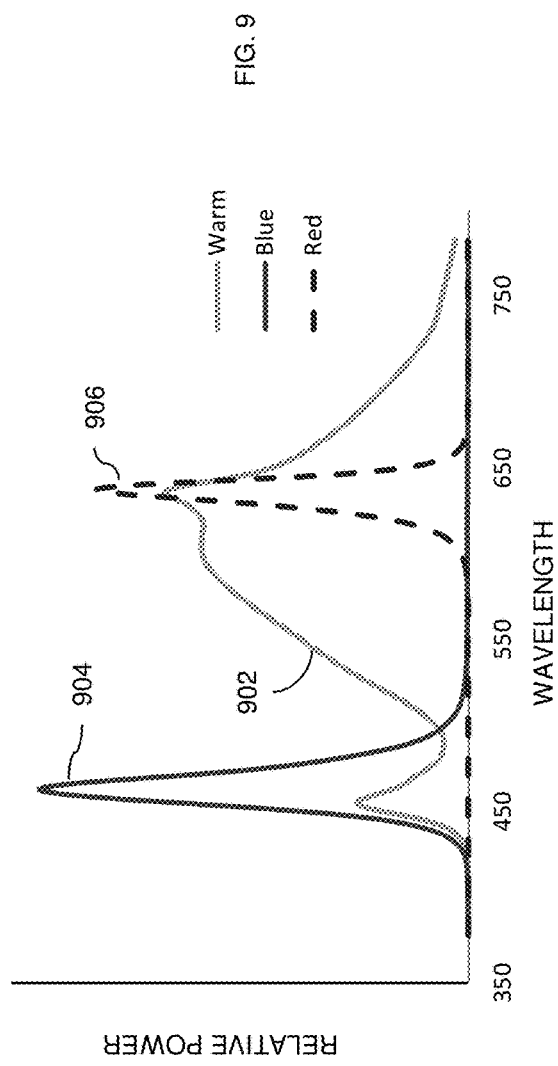
FIG. 9 is a graph illustrating examples of power distribution as function of wavelength for different prescribed lighting characteristics provided by the illuminance blankets shown in FIGS. 3A-3C and FIGS. 4A-4C, according to an aspect of the present invention.

FIG. 9 is a graph illustrating example spectral power distributions of various light panels 408, 408' for warm white light (902), blue light (904) and red light (906). Similar to LED strips 308 (310), one or more light panels 408, 408' among blue light panels 408-B, red light panel 408-R, cool white light panels 408 (408')-CW, warm white light panels 408-WW or a combination thereof may be activated to produce a desired color, distribution and intensity for a prescribed lighting characteristic.

Light panels 408, 408' on bottom surface 402 may be controlled by controller 108 (FIG. 1) to produce different prescribed lighting characteristics associated with different lighting tasks. Example prescribed lighting characteristics are shown further below in Table 2. It is understood that the arrangement of blue, warm white, red and cool white LEDs in FIG. 4A represents an example arrangement and that other arrangements of LEDs of different colors and/or intensity are possible.

Figure 5B:
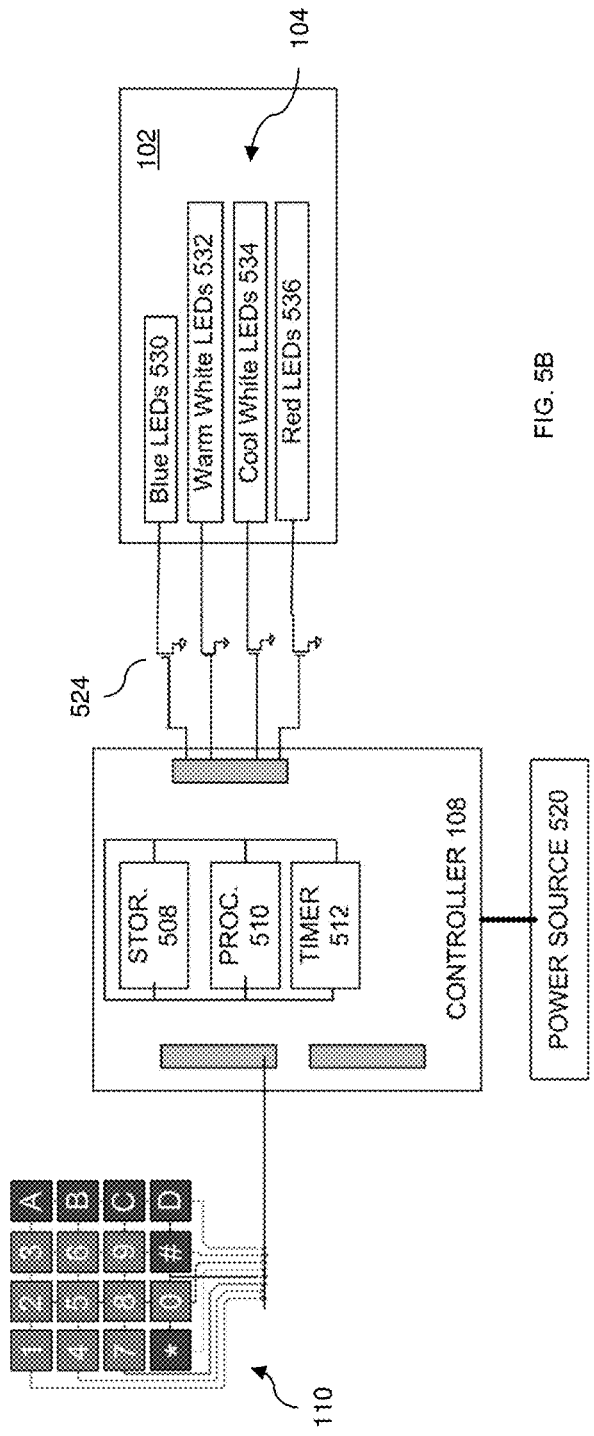
FIG. 5B is a functional block diagram of the controller shown in FIG. 5A illustrating example electrical connections between the controller, a user interface and light sources of an illuminance blanket, according to an aspect of the present invention.

Referring to FIGS. 5A and 5B, example controller 108 of lighting system 100 is shown. In particular, FIG. 5A is a functional block diagram of controller 108; and FIG. 5B is a functional block diagram of controller 108 illustrating example electrical connections between controller 108, user interface 110, power source 520 and example light sources 530-536 of illuminance blanket 102.

Controller 108 may include universal serial bus (USB) communication port 502, one or more input ports 504, power supply 506, storage 508, processor 510, timer 512 and one or more output ports 514. USB communication port 502, input port(s) 504, power supply 506, storage 508, processor 510, timer 512 and output port(s) 514 may be coupled together via data and control bus 516. Power supply 506 may be configured to power one or more components of controller 108.

In some examples, USB communication port 502 may be configured to receive data to program controller 108. In some examples, USB communication port 502 may be configured to receive and/or transmit signals and/or data to one or more other devices capable of USB communication. For example, USB port 502 may connect controller 108 to camera 106, an external storage device, a peripheral device (such as a keyboard, a pointing device, a printer), a personal computer, a laptop computer, a tablet computer, a mobile phone, etc. In some examples, camera 106 may be controlled via a wireless connection.

Input port(s) 504 may be configured to receive selections from user interface 110 indicating a lighting task or the prescribed lighting characteristic. Input port(s) 504 may also be configured to receive data indicating a prescribed lighting characteristic and corresponding lighting task. In some examples, the received data may be stored in storage 508 for controlling activation of light sources 104. Input port(s) 504 may be configured to receive analog input signals, digital input signals or a combination thereof.

Storage 508 may be configured to store prescribed lighting conditions and associated lighting tasks that are used by processor 510 to activate light sources 104. In some examples, the prescribed lighting conditions and associated lighting tasks may be stored in a look up table (LUT). In some examples, storage 508 may store one or more values for controlling capture and/or transmission of images from camera 106 (FIG. 1), including lighting conditions for visible light imaging and IR imaging. Storage 508 may store one or more values for USB communication port 502, input port(s) 504, power supply 506, processor 510, timer 512 and/or output port(s) 514. In some examples, storage 508 may store image(s)/audio information captured via camera 106 (FIG. 1). Storage 508 may include, for example, a RAM, a read only memory (ROM), a magnetic disk, an optical disc, flash memory or a hard drive. Storage 508 may be a memory, a magnetic disk, a database or essentially any local or remote non-transitory, tangible device capable of storing data.

Processor 510 may be configured to receive indications from user interface 110 indicating a prescribed lighting characteristic and activate one or more light sources 104 according to the prescribed lighting characteristic. In some examples, processor 510 may receive an indication of a lighting task from user interface 110 and may identify the corresponding prescribed lighting characteristic from a LUT stored in storage 508. In some examples, processor 510 may use a timing signal from timer 512 in order to control a timing and/or duration of light emission by light source(s) 104. In some examples, processor 510 may be configured to process image(s) and/or audio information received from camera 106 to provide an indication of the infant's behavior. In some examples, processor 510 may be configured to cause storage 508 (or storage 114 in FIG. 1) to store a verification and/or a time stamp (or time period) of the lighting characteristics of the light actually delivered by light sources 104. Processor 510 may be configured to control/implement USB communication port 502, input port(s) 504, power supply 506, storage 508, timer 512 and output port(s) 514. Processor 510 may be a conventional digital signal processor, a logic circuit or a microprocessor.

Timer 512 may be configured to produce a timing signal to control the activation onset and/or duration of the activation of one or more light sources 104. Timer 512 may be implemented by various conventional electronic components such as integrated circuits having an oscillation cycle.

Output port(s) 514 may be configured to receive one or more control signals from processor 510 and to generate one or more digital pulse-width modulation output signals 518 for activating light source(s) 104 according to a prescribed lighting characteristic.

It is understood that components of one or more of USB communication port 502, input port(s) 504, power supply 506, storage 508, processor 510, timer 512 and output port(s) 514 may be implemented in hardware, software or a combination of hardware and software.

In FIG. 5B, illuminance blanket 102 may include illuminance blanket 102 shown in FIGS. 3A-3C or illuminance blanket 102' shown in FIGS. 4A-4C. Blue LEDs 530, warm white LEDs 532, cool white LEDs 534 and red LEDs 536 represent example LEDs for producing different lighting characteristics associated with different lighting tasks.

In operation, power source 520 is used to provide power to power supply 506 of controller 108. User input is received by user interface 110 which indicates a selected lighting task (or prescribed lighting characteristic). The user indication from user interface 110 is received via input port(s) 504 of controller 108 and used to identify an associated prescribed lighting characteristic (for example, stored in storage 508). Processor 510 may generate one or more control signals to activate one or more of LEDs 530-536 according to the prescribed lighting characteristic. Processor 510 may control activation of one or more switches 524 (for example metal-oxide-semiconductor field-effect transistor (MOSFET) switches) according to the prescribed lighting characteristic (for selecting the appropriate LEDs among LEDs 530-536).

In general, controller 108 may control at least one of an intensity, a spectrum, a distribution, a timing or a duration of one or more of light sources 104 according to the prescribed lighting characteristic. For example, controller 108 may control at least one of activation of the number of light sources 104 (for light distribution control), the types of light sources that are activated (e.g., blue LEDs 530 and cool white LEDs 534, for a particular lighting task), the electrical power to light source(s) 104 (for intensity control) or the light transmission characteristic of diffuser material 318 (FIG. 3C) disposed on light sources 104.

Examples of prescribed lighting characteristics and associated lighting tasks are described next. In the first example (shown in Table 1), the total light output needed to achieve an average illuminance of 2000 lx was calculated as 1600 lm considering a Lambertian distribution and a distance $d_i$ of 35 cm from light sources 104 to the horizontal surface of the incubator (e.g., surface 203 in FIG. 2A). The example shown in Table 1 relates to illuminance blanket 102 shown in FIGS. 3A-3C. For a distance $d_i$ of 50 cm to bottom surface 203, for example, the total light output is about 2600 lm to achieve the same 2000 lx average illuminance. In general, the total light output may be determined based on the inverse square law (ISL), summarized below.

Using the ISL, the amount of light from a source may be specified in terms of luminous intensity (in units of candela (cd)), and the illumination (i.e., illuminance in units of lux (lx)) may be determined at different distances from the source. The inverse square law may be represented as:

$$E = \frac{I \cos \theta}{d^2} \tag{1}$$

where I is the intensity of the light source in the direction of the receiver, d is the distance from the light source to the receiver, $\theta$ is the angle measured from the surface normal at which light is incident on the receiver, and E is the illuminance at the receiver. As light propagates from a source it diverges and the same light covers a larger area. The area increases as the square of the distance.

Example spectral, spatial and temporal characteristics of the illuminance blanket 102 (FIGS. 3A-3C) (i.e., a prescribed lighting characteristic) for each of seven different lighting tasks are summarized in Table 1 below. In Table 1, CCT represents the correlated color temperature (i.e., the apparent color of the light emitted by a source relative to the color appearance of the light form an ideal incandescent source held at particular temperature and measured on the kelvin (K) scale), CRI is the color rendering index (i.e., a measure of the ability of the light generated by the light source to illuminate objects so they appear "natural" or "acceptable") and GAI is the gamut area index. The GAI is the gamut area (i.e., a measure of saturation provided by the light source) of eight test color samples defined in the CRI calculation, scaled by a factor to normalize the GAI of an equal energy spectrum to a value of 100. It is understood that the values in Table 1 represent an example of prescribed lighting characteristics for different lighting tasks and that other values for the spectral, spatial and temporal characteristics are possible, depending upon the configuration of illuminance blanket 102 and its distance from surface 203 (FIG. 2A).

TABLE 1

| Function (Lighting Task) | Spectral characteristics | | | Spatial Characteristics | | Control |
|---|---|---|---|---|---|---|
| | CCT | CRI | GAI | Light Level | Uniformity (avg. to min.) | |
| (1) Circadian entrainment-day/high setting | 3000K-5000K | >80 | 80-100 | 600 lx avg. | 4:1 | Adjustable ramp up time from 1 lx to 600 lx settings. Entrainment cycle length of 2.5 hours. |
| (2) Circadian entrainment-night/low setting | 3000K-5000K | >80 | 80-100 | 1 lx avg. | 4:1 | Adjustable ramp down time from 600 lx to 1 lx settings. Entrainment cycle length of 21.5 hours. |
| (3) Remote observation via camera, night | 3000K-5000K | >80 | | 1 lx | 4:1 | On/off |
| (4) In-room observation, general | 3000K-5000K | >80 | 80-100 | 60 lx | 4:1 | On/off |
| (5) In-room observation, medical procedures | 3000K-5000K | >80 | 80-100 | 2000 lx | 4:1 | On/off |
| (6) In-room observation, cyanosis | 3000K + red light | >80 | | 600 lx avg. | 4:1 | On/off |
| (7) In-room observation, vein contrast enhancement | 3000K + red light | ~50 | >110 | 600 lx avg. | 4:1 | On/off |

Figure 7:
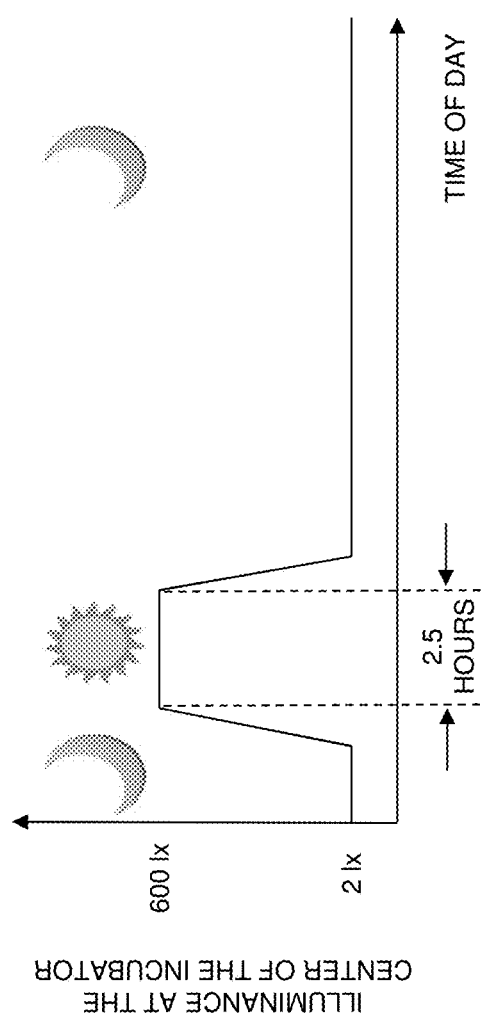
FIG. 7 is a graph of an example illuminance as a function of time for an illuminance blanket shown in FIG. 1 configured for circadian entrainment, according to an aspect of the present invention.

Circadian entrainment relates to lighting tasks 1 and 2 (in Table 1) and is also shown in FIG. 7. FIG. 7 is a graph of example illuminance as a function of time for circadian entrainment. During a day (high) setting, the light level is set to a high level (e.g., about 600 lx) for an example 2.5 hour period of time. During a night (low) setting, the light level is set to a low level (e.g., about 1 lx) for an example 21.5 hour period of time. In an example, controller 108 may include a ramp up time (task 1) and/or a ramp down time (task 2) for gradually increasing/decreasing the light level. In a non-limiting example, the ramp up/ramp down time is about 1 minute. In some examples, the ramp up/down time may be adjusted.

Task 3 in Table 1 illustrates an example prescribed lighting characteristic for remote observation via camera 106 (FIG. 1) during a night (low visible light) setting. For example, camera 106 may be configured to perform IR imaging during the night setting. During the daytime (i.e., with sufficient visible light), camera 106 may capture one or more images via visible light imaging, according to the prescribed lighting characteristics shown in one or more of tasks 1, 4, 6 or 7. It is understood that the prescribed lighting characteristic may vary depending upon the sensitivity of a specific camera 106.

Task 4 in Table 1 illustrates an example prescribed lighting characteristic for general in-room observation. An example spectral power distribution of light sources 104 that may be suitable for general in-room observation includes a CCT of about 3860 K, a CRI of about 86, and a GAI of about 87 measured from an example illuminance blanket 102 producing an illuminance of about 602 lx at the center of the incubator from a distance of about 35 cm.

Task 5 in Table 1 illustrates an example prescribed lighting characteristic for in-room observation during medical procedures (e.g., such as catheter insertion), which may require higher light levels and diffused (shadow-free) light.

Task 6 in Table 1 illustrates an example prescribed lighting characteristic for in-room observation for cyanosis (a bluish discoloration of the skin resulting from poor circulation or inadequate oxygenation of blood). The accuracy of clinical detection of cyanosis has been shown to improve with the use of light sources that have significant emission around 660 nm. However, whereas sources with too little emission in the 660 nm region can result in false positive results, sources with too much emission can result in failure to detect cyanosis. The reason for this is that detecting cyanosis depends on color contrast, thus the complete spectral distribution of the source needs to be considered. Standards Australia developed a test method and metric to evaluate the effectiveness of light sources for clinical observation of cyanosis. Publication AS 1680.2.5 (1997) defined the cyanosis observation index (COI) as a function of the spectral power distribution of the light source, a reference illuminant, and the spectral characteristics of blood with 50% and 100% oxygen saturation. COI is a dimensionless figure that results from averaging the color difference between the reference light source (4000 K blackbody radiator) and the test source, for each oxygen saturation criterion. Compliance with AS 1680.2.5 (1997) requires light sources used in clinical observation in health care facilities to have both a CCT between 3300 K and 5500 K and a COI equal or lesser than 3.3.

Task 7 in Table 1 illustrates an example prescribed lighting characteristic for in-room observation for vein contrast enhancement. Typically, red narrow band light sources (e.g., 630 nm peak wavelength LEDs) are used for vein detection in trans-illumination devices.

The second example (shown in Table 2) assumes a 50 cm distance $d_i$ to surface 203 (FIG. 2A) and relates to illuminance blanket 102' shown in FIGS. 4A-4C. In this example, the total light output needed to achieve an average illuminance of 600 lx at the center of an incubator from a distance of 50 cm was estimated at about 800 lm, considering a Lambertian distribution. The luminance of the illuminance blanket 102' is approximately 1200 cd/m². As with Table 1, it is understood that the values in Table 2 represent an example of prescribed lighting characteristics for different lighting tasks and that other values for the spectral, spatial and temporal characteristics are possible, depending upon the configuration of illuminance blanket 102' and its distance from surface 203 (FIG. 2A).

Thus, in some examples, camera 106 may be configured to capture daytime (visible light) images and nighttime (IR) images. Camera 106 may be configured to transmit images 612 to be displayed on display device 110 over a wired connection and/or a wireless connection. In some examples, camera 106 may be configured to communicate over the Internet to display device 110 (such as via Wi-Fi 610). In some examples, camera 106 may include optional microphone 605 configured to capture audio information from an infant. In one example, camera 106 includes model DCS-932L wireless day/night home network camera manufactured by D-Link Corporation (Taipei, Taiwan).

Figure 10:
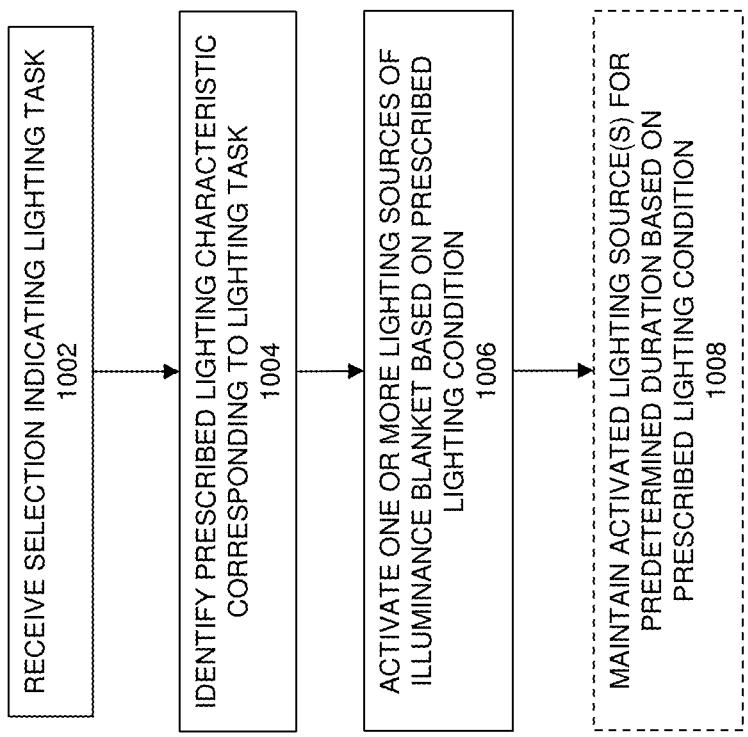
FIG. 10 is a flow chart illustrating an example method of controlling light emission of an illuminance blanket for various lighting tasks, according to an aspect of the present invention.

Referring to FIG. 10, a flow chart is shown of an example method of controlling light emission of illuminance blanket 102, 102' for various lighting tasks. At step 1002, a selection is received by controller 108 (FIG. 1) indicating a lighting task to be performed. For example, controller 108 may

TABLE 2

| Function (Lighting Task) | Spectral characteristics | | | Spatial Characteristics | | Control |
| --- | --- | --- | --- | --- | --- | --- |
| | CCT | CRI | GAI | Light Level | Uniformity (avg. to min.) | |
| (1) Circadian entrainment-day/high setting | 3000K-5000K | >80 | 80-100 | 600 lx avg. | 4:1 | Adjustable ramp up time from 1 lx to 600 lx settings. Entrainment cycle length of 2.5 hours. |
| (2) Circadian entrainment-night/low setting | 3000K-5000K | >80 | 80-100 | 6 lx avg. | 4:1 | Adjustable ramp down time from 600 lx to 1 lx settings. Entrainment cycle length of 21.5 hours. |
| (3) Remote observation via camera, night | 3000K-5000K | >80 | | 6 lx | 4:1 | On/off |
| (4) In-room observation, general | 3000K-5000K | >80 | 80-100 | 60 lx | 4:1 | On/off |
| (5) In-room observation, cyanosis | 3000K + red light | >80 | | 600 lx | 4:1 | On/off |
| (6) In-room observation, vein contrast enhancement | 3000K + red and blue light | ~50 | >110 | 600 lx avg. | 4:1 | On/off |
| (7) Circadian entrainment-with blue light | | | | 30 lx | 4:1 | Adjustable ramp rate, circadian entrainment day/night cycles |

Tasks 1-6 in Table 2 for illuminance blanket 102' are similar to tasks 1-4, 6 and 7 described above in Table 1, except for differences in the CCT and light levels. Illuminance blanket 102' does not include a medical procedure task (task 5 in Table 1). Task 7 in Table 2 provides an example of using blue light (e.g., with maximum wavelength of about 470 nm) for performing circadian entrainment.

Referring to FIG. 6, a functional block diagram of camera 106 is shown. FIG. 6 illustrates an example wireless connection between camera 106 and display device 110 via Wi-Fi hot spot 610. Camera 106 having camera body 606 may include lens 602 having an IR filter and night vision IR LEDS 604. Camera 106 may also include power supply 608.

receive user input entered via user interface 110. At step 1004, controller 108 may identify a prescribed lighting characteristic corresponding to the indicated lighting task. For example, controller 108 may identify the prescribed lighting task from a LUT stored in storage 508 (FIG. 5A).

At step 1006, controller 108 may activate one or more light sources 104 disposed on illuminance blanket 102, 102' such that light source(s) 104 emit light according to the prescribed lighting characteristic (identified in step 1004). At optional step 1008, controller 108 may activate lighting source(s) 104 for a predetermined duration (according to the prescribed lighting characteristic), for example, using timer 512 (FIG. 5A). For example, optional step 1008 may be used for circadian entrainment. In some examples, step 1006 and/or step 1008 may be activated at a predetermined onset time (based on the prescribed lighting characteristic).

Although the invention has been described in terms of multipurpose lighting systems and methods of controllable incubator lighting for multiple lighting tasks, it is contemplated that one or more steps and/or components may be implemented in software for use with microprocessors/general purpose computers. In this embodiment, one or more of the functions of the various components and/or steps described above may be implemented in software that controls a computer. The software may be embodied in non-transitory tangible computer readable media (such as, by way of non-limiting example, a magnetic disk, optical disk, hard drive, etc.) for execution by the computer. As described herein, devices 106, 108, 110, 112 and 114, shown in FIG. 1, may perform certain operations using dedicated circuitry and/or using software contained in a computer-readable medium. The software instructions may cause controller 108 to perform one or more processes described herein. Alternatively, hardwired circuitry may be used in place of, or in combination with, software instructions to implement processes described herein. Thus, implementations described herein are not limited to any specific combination of hardware circuitry and software.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A lighting system comprising:
    a sheet of flexible material;
    a plurality of light sources attached to the sheet of flexible material;
    a transparent cover disposed over the sheet of flexible material;
    a transparent cushioning material positioned between the plurality of light sources and the transparent cover;
    a diffusion material positioned between the plurality of light sources and the transparent
    cover such that the lighting system is configured to emit diffused light;
    a controller coupled to the plurality of light sources, the controller configured to control one or more of the plurality of light sources according to one of a plurality of prescribed lighting characteristics associated with a respective plurality of different lighting tasks; and
    a camera coupled to the sheet of flexible material in a vicinity of the plurality of light sources, the camera configured to capture one or more images of an object positioned within an incubator synchronously with the light emitted by the one or more of the plurality of light sources;
    wherein the sheet of flexible material is configured to be removably disposed on the incubator such that the emitted diffused light is transmitted into the incubator.

2. The lighting system of claim 1, wherein each prescribed lighting characteristic includes at least one of a predetermined intensity, a predetermined spectrum, a predetermined distribution, a predetermined duration or a predetermined timing.

3. The lighting system of claim 1, wherein the plurality of different lighting tasks includes at least one of circadian entrainment, illumination for remote viewing of the object, shadow-free illumination for local viewing of the object, chromatically-enhanced illumination for examination of the object, or illumination for a medical procedure.

4. The lighting system of claim 1, wherein the camera is configured to capture one or more images within at least one of a visible light spectrum or an infrared (IR) light spectrum.

5. The lighting system of claim 1, further comprising a display device coupled to the camera via a wired connection or a wireless connection.

6. The lighting system of claim 1, further comprising a user interface coupled to the controller, the user interface configured to receive a selection for the one of the plurality of prescribed lighting characteristics.

7. The lighting system of claim 1, wherein the sheet of flexible material includes a first side and a second side opposite the first side, the plurality of light sources being attached to the first side, the second side or a combination thereof.

8. The lighting system of claim 1, wherein the plurality of light sources includes at least two subsets of light sources, the at least two subsets of light sources configured to emit the light with at least one of different spectral characteristics or different intensities.

9. The lighting system of claim 8, wherein the controller is configured to control at least one of selection of a number of light sources among the plurality of light sources, selection of one or more subsets of light sources among the at least two subsets of light sources, an amount of power distributed among the plurality of light sources, an onset of the emitted light or a duration of the emitted light.

10. The lighting system of claim 1, wherein the transparent cover is formed of a skid resistant material.

11. A method of providing controllable lighting, the method comprising the steps of:
    positioning an illuminance blanket over a top surface of an incubator and emitting diffused light into the incubator from above;
    receiving, by a controller, an indication of a lighting task to be performed via the illuminance blanket, the illuminance blanket including a plurality of light sources attached to a sheet of flexible material, a transparent cover disposed over the sheet of flexible material, a transparent cushioning material positioned between the plurality of light sources and the
    transparent cover, and a diffusion material positioned between the plurality of light sources and
    the transparent cover such that the illuminance blanket is configured to emit diffused light;
    identifying, by the controller, a prescribed lighting characteristic associated with the indicated lighting task from among a plurality of prescribed lighting characteristics associated with a respective plurality of different lighting tasks; and
    controlling one or more of the plurality of light sources of the illuminance blanket to emit diffused light according to the identified prescribed lighting characteristic; and
    capturing, via a camera coupled to the sheet of flexible material in a vicinity of the plurality of light sources, one or more images of an object positioned within the incubator synchronously with the light emitted by the one or more of the plurality of light sources.

12. The method of claim 11, wherein each prescribed lighting characteristic includes at least one of a predetermined intensity, a predetermined spectrum, a predetermined distribution, a predetermined duration or a predetermined timing.

13. The method of claim 11, wherein the controlling of the one or more of the plurality of light sources includes controlling at least one of selection of a number of light sources among the plurality of light sources, an amount of power distributed among the plurality of light sources, an onset of the emitted light or a duration of the emitted light.

14. The method of claim 11, further comprising capturing, via a microphone, audio information received from the object.

15. The method of claim 14, further comprising storing, in non-transitory storage, at least one of the audio information or the one or more images.

16. The method of claim 11, further comprising storing, in non-transitory storage, at least one of a verification that the identified prescribed lighting characteristic lighting has been emitted or a timestamp indicating when the identified prescribed lighting characteristic was emitted.

17. The method of claim 11, wherein the plurality of different lighting tasks includes at least one of circadian entrainment of the infant, illumination for remote viewing of the infant, shadow-free illumination for local examination of the infant, illumination for a medical procedure, and chromatically-enhanced illumination for at least one of cyanosis observation or vein enhancement.

18. The method of claim 17, wherein the controlling of the one or more of the plurality of light sources includes controlling a timing, a duration and an intensity of the emitted diffused light to promote the circadian entrainment of the infant.

19. The method of claim 17, wherein the plurality of different lighting tasks includes at least one of illumination for remote viewing of the infant, shadow-free illumination for local examination of the infant, and illumination for a medical procedure, wherein the illumination for the medical procedure has a higher intensity than the shadow-free illumination for the local examination of the infant and the illumination for the remote viewing of the infant.

20. An illuminance blanket comprising:
a flexible cover having a top layer and a bottom layer joined together at peripheral edges thereof and at a plurality of joints to form a plurality of internal compartments, each of the plurality of joints extending transverse to either a length or a width of the flexible cover;
a plurality of light sources configured to emit diffused light integrated within the flexible cover, at least one of the plurality of light sources is positioned within each of the plurality of internal compartments;
a camera integrated within one of the plurality of internal compartments of the flexible cover, the camera configured to capture one or more images of an object positioned within an incubator synchronously with the light emitted by the one or more of the plurality of light sources;
wherein the bottom layer of the flexible cover comprises a plurality of apertures, the apertures configured for exposing the camera and the plurality of light sources;
a controller coupled to the plurality of light sources, the controller configured to control one or more of the plurality of light sources according to one of a plurality of prescribed lighting
characteristics associated with a respective plurality of different lighting tasks;
the flexible cover is foldable along the plurality of joints such that the illuminance blanket is configured to be removably disposed on at least portions of a top surface and one or more side surfaces of the incubator such that the emitted diffused light is transmitted into the incubator.

21. The illuminance blanket of claim 20, further comprising:
a display device coupled to the camera; and
a user interface coupled to the controller, the user interface configured to receive a selection for the one of the plurality of prescribed lighting characteristics.

* * * * *